United States Patent [19]

Bell et al.

[11] 4,423,155

[45] Dec. 27, 1983

[54] DIMETHYL ETHER SYNTHESIS CATALYST

[75] Inventors: Weldon K. Bell, Pennington; Clarence D. Chang, Princeton, both of N.J.

[73] Assignee: Mobil Oil Corporation, New York, N.Y.

[21] Appl. No.: 236,472

[22] Filed: Feb. 20, 1981

[51] Int. Cl.³ .................. B01J 21/04; B01J 23/06; B01J 23/72

[52] U.S. Cl. ................... 502/38; 502/73; 502/208; 502/244; 502/302; 502/342

[58] Field of Search ............ 252/416, 463, 437, 454, 252/455 R, 455 Z, 462; 518/713

[56] References Cited

U.S. PATENT DOCUMENTS

| | | | |
|---|---|---|---|
| 3,790,505 | 2/1974 | Casey et al. | 252/463 |
| 3,925,258 | 12/1975 | Cox | 252/416 X |
| 3,988,259 | 10/1976 | Ray | 252/416 |
| 4,011,275 | 3/1977 | Zahner | 518/714 |
| 4,098,809 | 7/1978 | Pagani | 518/713 |
| 4,111,847 | 9/1978 | Stiles | 252/463 |
| 4,126,581 | 11/1978 | Sugier et al. | 252/463 |
| 4,177,167 | 12/1979 | Manara et al. | 252/455 R |

FOREIGN PATENT DOCUMENTS

278353 3/1929 United Kingdom.
1159035 7/1969 United Kingdom.

OTHER PUBLICATIONS

Herman et al., *Catalytic Synthesis of Methanol from CO/H₂*, J. of Catalysis, 56, pp. 407-429 (1979).

*Primary Examiner*—W. J. Shine
*Attorney, Agent, or Firm*—Alexander J. McKillop; Charles J. Speciale; L. B. Wise

[57] ABSTRACT

A new catalyst and process for synthesis of dimethyl ether from low $H_2/CO$ ratio syngas are disclosed. The catalyst is a combination of Cu, Zn and Al, co-precipitated in predetermined relative amounts, which is found to be oxidatively regenerable and utilizable with the syngas product of modern coal gasifiers without the need for external water-gas-shift.

8 Claims, 1 Drawing Figure

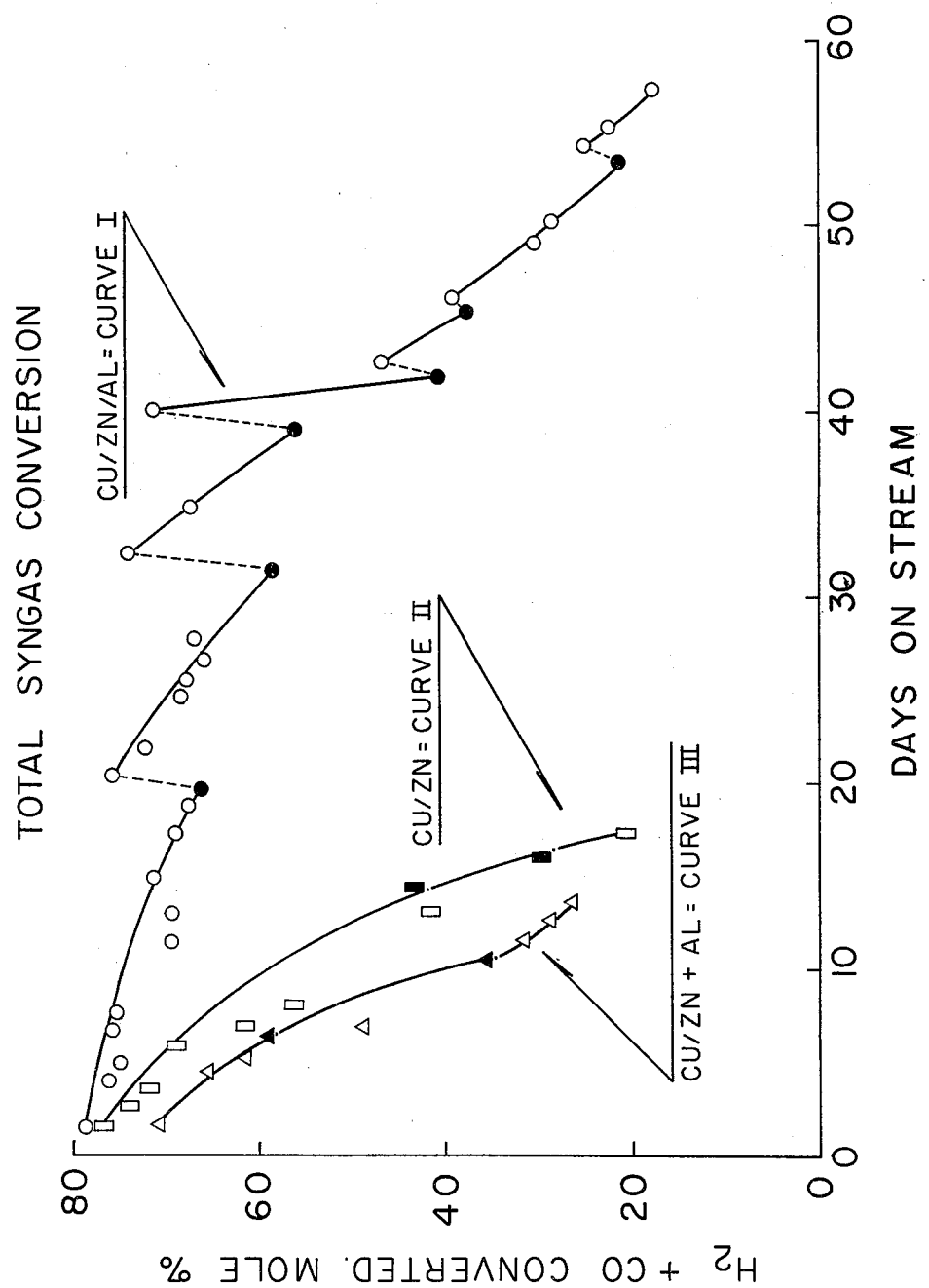

DIMETHYL ETHER SYNTHESIS CATALYST

BACKGROUND OF THE INVENTION

1. Field of the Invention

This invention is concerned with a process for converting synthesis gas ($H_2$ and CO) to dimethyl ether. It is also concerned with a novel catalyst composition for effecting the conversion reaction.

2. Discussion of the Prior Art

There are at present two major routes for effecting the conversion of coal via synthesis gas to liquid fuels comprising the well publicized Fischer-Tropsch process and a more recently developed methanol to gasoline process such as provided in U.S. Pat. No. 3,928,483, issued Dec. 23, 1975. The Fischer-Tropsch process produces a wide range of $C_1$ to $C_{50}$ products comprising gases, liquid hydrocarbons, oxygenates and water.

Common to each of the above processes is the overriding influence of the capital cost of synthesis gas ($H_2$+CO) production. This varies with gasifier design, which is in turn influenced by coal properties and product enthalpy. A recent review of gasifier technology has identified some high efficiency gasifiers which of necessity produce synthesis gas having relatively low ratios of $H_2$/CO resulting from utilizing low ratios of steam and oxygen in the gasification operation. Thus, the most recent advanced gasifiers operate at temperatures requiring relatively low product recovery temperatures and low steam to carbon ratios which translate into high thermal efficiency. The "syngas" produced under these conditions may have a ratio equal to 1 and more usually, for the highest efficiency gasifiers, a ratio of less than 1 and within the range of about 0.4 to about 0.7. Such low ratio syngas cannot be directly utilized by the present day conventional Fischer-Tropsch operations and methanol synthesis processes, both of which require $H_2$/CO ratio equal to or greater than 2. Any external water-gas shift operation to increase a low ratio syngas of 1 or less up to 2 or more would substantially cancel any gains in efficiency achieved by the most advanced high efficiency gasifiers.

A principal advantage to be gained in producing dimethyl ether (DME) directly from syngas is that it has been found that this compound can be readily converted to gasoline range hydrocarbons using a special class of crystalline porotectosilicates, represented by ZSM-5 crystalline zeolite such as discussed in U.S. Pat. No. 3,928,483, wherein the formed methanol is dehydrated and the ether product thereof is converted over said ZSM-5 crystalline zeolite.

Prior to our present discovery, two patents dealing with synthesizing DME directly were known. These include British Pat. No. 278,353 (1926) to F. R. Bechowsky and German Offen. No. 2362944 (1974) to G. Pagani. The British patent claims a process for producing DME by contacting synthesis gas ($H_2$+CO) with a hydrogenating catalyst and a dehydrating catalyst at elevated temperatures and pressure. In this patent, DME synthesis was obtained in the absence of the known shift reaction. In the second or German patent, the catalyst comprised a methanol synthesis component and a dehydrating component. In one example, a gas with $H_2$/CO ratio of 0.86 was contacted with a catalyst comprising Cu/Zn/Cr, in an atomic ratio of 82/16/4 and supported on alumina, at 482° F. and 1422 psia. The conversion of the syngas was 77%. The exit gas contained 24.2% DME, 0.91% MeOH, 27.3% $CO_2$, 0.41% $H_2$, 0.54% $CH_4$, with the balance being $H_2$, CO and $N_2$.

In more recent work, Sherwin and Blum reported in an Interim Report for May 1978 under the title "Liquid Phase Methanol", prepared for Electric Power Research Institute, Palo Alto, Calif., the attempt to produce DME by adding gamma-alumina and 13X molecular sieve to a slurry reactor system containing a commercial methanol synthesis catalyst. At 446° F.–572° F., 515–1015 psia and 2015–6915 GHSV, only traces of DME were observed. A catalyst comprising Cu/Zn/Cr, in an atomic ratio of 6/3/1 impregnated on Davidson 980 $SiO_2$/$Al_2O_3$, produced trace amounts of DME at 446° F., 1015 psia and 2000 GHSV. The feed charged in the above experiments contained 50% $H_2$, 25% CO, 10% $CO_2$ and 15% $CH_4$.

SUMMARY OF THE INVENTION

The present invention is directed to the conversion of synthesis gas or "syngas" to intermediate products which are readily convertible to gasoline boiling range hydrocarbons. The direct conversion of syngas to dimethyl ether is technically feasible. Furthermore, the conversion of dimethyl ether to gasoline boiling range products comprising olefins and aromatics is likewise achievable, as identified above, by employing the particular class of crystalline zeolite discussed therein and below.

In a more particular aspect, the present invention is concerned with improvements in the direct conversion of syngas to dimethyl ether whereby an economically attractive operation is attained by virtue of reducing the catalyst aging characteristics, in cooperation with utilization of an oxidative regeneration technique which has not heretofore been successful, and thus maintaining the catalyst at a high level of activity sufficient to sustain below or near equilibrium conversion level of the syngas feed.

The syngas conversion operation of this invention relies upon using the metal components of a methanol synthesis catalyst in a particularly selective relationship, fulfilling herein described restricting parameters of hydrogenating components, in combination with an acidic dehydrating component. More particularly, the catalyst compositions of the present invention rely upon the technique of coprecipitation of the hydrogenating components, either alone or mixed with the dehydrating component, wherein the atomic ratio of the hydrogenating components (Cu, Zn and Al) may be varied within the relatively narrow limits herein specifically identified. More particularly, coprecipitated components of Cu, Zn and Al are used in a ratio with respect to one another such that the ratio of Al/(Cu+Zn) is at least 0.1:1 and preferably at least 0.2:1, normally between 0.1:1 and 2:1. A ratio of 0.2 to 0.7 is particularly preferred. On the other hand, the ratio of Cu/Zn is preferably within the range of 0.2 to 5.0.

The acidic dehydrating component of the catalyst composition may be selected from the group consisting of gamma-alumina, silica-alumina, ZSM-5 type crystalline zeolites having high $SiO_2$ content, phosphates, titanium oxide in combination with silicon oxide, rare earths and clays. Of these compositions, it is particularly preferred to use gamma-alumina in an amount comprising about 50% of the catalyst composition.

The (DME) dimethyl ether synthesis techniques of this invention are of particular and novel interest upon noting that $H_2$/CO ratio gases of either less than 1 or greater than 1 can be utilized. Thus, the ratio of $H_2/CO$ may be within the range of 0.4 to 3. However, it is particularly preferred to employ gas ratios equal to or less than 1, since such gas ratios are much more economically produced by modern high efficiency gasifiers and such a source of syngas can result in from 30% to 40% overall reduction in processing costs. In this low ratio ($H_2/CO$) syngas operating environment, it has been determined that the hydrogen ($H_2$) deficiency of the low ratio syngas, in the range of 0.4 to 0.7, can be remedied or compensated for by injecting steam ($H_2O$) into the catalyst mass separately or in admixture with the low ratio syngas charged. This added steam ($H_2O$) is subject to water-gas-shift reaction by the particular catalyst composition employed, resulting in a very effective and increased $H_2/CO$ ratio gas in the catalyst reaction zone. This particular operating mode thus eliminates the need for external water-gas-shift requirements to modify the low ratio syngas, thereby further contributing to the overall economic improvement of the processing combination.

The present investigation into obtaining direct conversion of syngas to dimethyl ether (DME), and the concepts developed therefrom, dramatically demonstrate that certain selected catalyst compositions, consisting of coprecipitated mixed oxides of Cu, Zn and Al and mixed with a suitable acid component such as gamma-alumina, provide high catalyst activity and selectivity for effecting dimethyl ether synthesis. More important, however, was the discovery that these selected coprecipitated catalyst compositions could be periodically oxidatively regenerated to maintain desired high catalyst activity. That is, the particular catalyst compositions of the invention were maintained at high steady state activity for an extended on-stream syngas conversion operating period by relying upon particular oxidative regeneration and pretreatment techniques of relatively short duration as more particularly discussed herein. For example, the catalyst in the syngas reaction zone may be regenerated therein or it may be passed through a separate catalyst regeneration operation and then returned to the reaction zone to maintain desired catalyst activity and selectivity. The regeneration of the catalyst may be accomplished in a continuous, semi-continuous or an interrupted (e.g. periodic) operating mode, depending upon whether a fixed bed or a moving catalyst system is employed.

BRIEF DESCRIPTION OF THE DRAWING

The drawing FIGURE is a graphical representation of the comparative examples provided hereinafter. The curves illustrate the performance and oxidative regenerability of the Cu/Zn/Al catalyst of this invention, as compared to a Cu/Zn coprecipitated catalyst and a Cu/Zn catalyst admixed with $Al_2O_3$ by "high shear" mixing technique.

DESCRIPTION OF SPECIFIC EMBODIMENTS

As disclosed above, we have now discovered a catalyst system which is found to be useful in promoting direct conversion of synthesis gas, i.e. hydrogen and carbon monoxide, to dimethyl ether. An especially desirable characteristic of these catalysts, which contain both methanol synthesis/water-gas-shift and acid dehydration components, is that they are oxidatively regenerable, thereby prolonging their useful lives well beyond that of other, non-regenerable, catalysts.

The methanol synthesis/water-gas-shift component of the novel catalyst system comprises a Cu/Zn/Al catalyst prepared by coprecipitation of copper, zinc and aluminum from a common solution. A preferred method of preparation of the catalyst comprises dissolving nitrate salts of the metal components, in the desired molar ratios and concentrations, in aqueous solvent and subsequently adding excess sodium carbonate thereto and precipitating the metal carbonates. The precipitate is then recovered, washed to remove soluble nitrates and carbonates, dried and calcined. Of course, it is to be understood that other soluble salts of the metal components may be utilized in place of the nitrate salts and that the precipitate may take the form of something other than the carbonate. Likewise, solvents other than water may be employed. The important parameter is that the metal components first be mixed in the desired molar ratios, in solution, and then co-precipitated to form a solid containing those components. The subsequent calcination step will oxidize the metals to their respective oxides.

The dehydrating component of the catalyst is preferably an acidic matrix material selected from materials such as gamma alumina, porotectosilicates including clays and natural or synthetically prepared crystalline aluminosilicates, and zeolites. Especially preferred are gamma alumina and crystalline zeolites having a constraint index within the approximate range of 1–12 and a high silica content. Other useful dehydrating components include, but are not limited to, phosphates, titanium oxide in combination with silicon oxide, rare earths and clays.

The methanol synthesis and dehydration components of the catalyst system are combined by physical mixing of powders of the two components, either dry or in a slurry, followed by pelleting or extrusion, as appropriate. An inert or acidic binder might be included in the mixture to improve pellet/extrudate physical properties. Approximately 5 to 95 wt % of the combination catalyst should comprise the dehydration component thereof, although it will be preferred to utilize from 20% to 70% dehydration component, based on the weight of the combination catalyst, excluding binder.

It has been found that both the methanol synthesis component and the combined catalyst system described above are oxidatively regenerable, thereby significantly extending the useful life of the catalyst beyond the expectations of the art based on experience with previous catalysts. Regeneration may be accomplished periodically or continuously, depending on whether a fixed or moving catalyst system is employed. The basic technique for regenerating a spent catalyst is to pass an oxygen-containing gas over the catalyst while heating to elevated temperature within the range of 250° C. to 540° C., it being preferred to employ temperatures below about 540° C. for any extended operating period. The regeneration is continued for a relatively short duration contact time or until there is a breakthrough of the charged oxygen-containing gas.

Following oxidation or regeneration of the catalyst, it has been found to be important, if not essential, to avoid contacting the freshly oxidized catalyst with a high-temperature reducing gas (e.g. $H_2$). That is, reducing the freshly regenerated catalyst with hydrogen or any other hydrogen-rich reducing gas as should be avoided, particularly where the contact temperature equals or exceeds 260° C. It is preferred, therefore, to contact the oxygen regenerated catalyst with a reducing gas such as a syngas feed or a diluted syngas at a temperature which, initially, is within the range of 175° C. to about 235° C. and thereafter to raise the temperature and/or change the composition of the syngas feed to achieve near thermodynamic yields of DME.

As mentioned above, dimethyl ether synthesis offers decided advantages over other Fischer-Tropsch and methanol synthesis operations, since it particularly lends itself to utilizing a relatively low ratio syngas, e.g. $H_2/CO=1$, with high selectivity to products convertable to liquid fuels or chemicals. This particular operation can be used to advantage in combination with any of the new high efficiency gasifying operations producing low ratio syngas of less than 1 by the injection or addition of water (steam) with the low ratio syngas feed passed in contact with the catalysts of this invention and suitable for DME synthesis. In this novel operation, the water-gas-shift capability of the catalyst is used to advantage. The DME produced may subsequently be converted to gasoline boiling range hydrocarbons by contact with ZSM-5 or similar crystalline zeolite material by methods described in numerous U.S. Patents.

In an effort to illustrate some of the embodiments of this invention, and the advantages thereof over prior art practices, the following experiments were carried out:

EXAMPLE 1—PREPARATION OF CU/ZN/AL CO-PRECIPITATED CATALYST

To an aqueous solution of the nitrates of aluminum, copper and zinc, in molar amounts of 0.115, 0.12 and 0.12 respectively, was added an aqueous solution of 1.05 moles of sodium carbonate. The precipitation was carried out at 85° C.-90° C. with agitation. The precipitate was cooled, filtered, washed and extracted with water to remove soluble nitrates and carbonates, and then dried in a vacuum oven and calcined for 6 hours at about 280° C.

The dimethyl ether catalyst was prepared by combining equal weights of the above calcined powder and a powdered gamma-alumina, pelletizing the resultant mixture and crushing the pellets to 10–30 mesh.

EXAMPLE 2—PREPARATION OF CU/ZN CO-PRECIPITATED CATALYST

Using the procedure of Example 1, a co-precipated Cu/Zn catalyst, wherein the copper and zinc were at a ratio of 1/1, was prepared. The co-precipitated Cu/Zn pair was recovered, washed and dried as above and then calcined at 343° C.

The DME catalyst was prepared by combining equal weights of the calcined Cu/Zn powder with a powdered gamma-alumina. The mixture was then pelletized and sized as in Example 1.

EXAMPLE 3—PREPARATION OF CU/ZN//AL MIXED CATALYST

Mixed 2 parts by weight of the Cu/Zn co-precipitated pair prepared in Example 2 with 1.5 parts by weight of aluminum oxide and suspended the mixture in water. These were mixed in blender to prepare a high shear slurry. The mixed solid was recovered as above and calcined. This is essentially the preparation disclosed in U.S. Pat. No. 3,790,505 issued to Casey et al. The ratios of the metal components Cu/Zn//Al were 1/1//1.5, respectively.

The foregoing Cu/Zn//Al high shear mixture was then further mixed with powdered gamma alumina on an equal weight basis, pelletized and sized as in Examples 1 and 2.

To obtain experimental evidence of this invention, a microreactor with related system components was designed which permitted rapid catalyst loading and pretreatment and ready adjustment of reaction conditions, feed gas mixtures and regeneration conditions without disturbing the catalyst. The reactor was 40 centimeters in length and was made from a 3/8 inch OD 304 stainless steel (SS) tube with an annular 1/8 inch OD 304 SS thermowell running the entire length of the bed of catalyst therein. A 3.0 cc catalyst bed (9 cm long) was centrally positioned in a 30 cm vertical tube furnace. The catalyst bed was held in place by Vycor glass wool supported by Pyrex tubes filling the reactor voids. Temperature was maintained by a proportional band controller with a thermocouple located in the furnace wall near the reactor. During use, premixed $H_2$ and CO were compressed and fed through activated charcoal traps. The charcoal was necessary to remove traces of iron carbonyl present in the feed gas cylinders. Constant gas flow was maintained by a thermal mass flow controller and reactor pressure was maintained by a back-pressure regulator downstream of the reactor and liquid traps.

All catalysts were initially pretreated in the reactor at 204° C. in an $H_2/N_2$ stream (1 atm., GHSV=1500) the hydrogen composition of which was slowly increased from 0 to 2 volume percent, then to 8.5%.

The catalyst was cooled in an inert gas stream to a temperature below 49° C., the reactor feed switched to synthesis gas at the space velocity and pressure of the run, and temperature then increased.

Typical run conditions were $H_2/CO$ feed ratio=1/1, 100 atm., 315° C., and GHSV=4000.

Oxidative regeneration of the catalyst was carried out as follows:

1. Depressurize the reactor to atmospheric pressure and flush in helium.
2. Elute a pulse of 100% oxygen from a container of volume 100 liter/liter catalyst (i.e. 100 liters $O_2$ at STP/liter catalyst) at 1 atmosphere pressure with helium at a GHSV of about 600 and temperatures of between about 288° C. and 343° C.
3. Flush and pressurize the system to 100 atm. with helium.
4. Bring synthesis gas into the reactor to resume reaction at 315° C. and 100 atm. by passing a 100% syngas stream to the reactor through a buffer container of helium at 100 liters per liter of catalyst and at a GHSV of 4000.

EXAMPLES 4–6

Using the reactor system described above, each of the catalysts of Examples 1-3 was brought into contact with a syngas feed stream ($H_2/CO=1/1$) at 316° C. (600° F.), $10^7$ Pa (100 atm) and GHSV=4,000. The reactor effluent was analyzed periodically to determine the level of syngas conversion and attempts were made to oxidatively regenerate each of the respective catalysts during the runs. The results are illustrated in the attached drawing.

Curve I represents the behavior of the Cu/Zn/Al co-precipitated catalyst of Example 1. The run was followed for 60 days and the solid points on the curve indicate the oxidative regenerations of the catalyst.

Curve II shows the performance of the Cu/Zn co-precipitated catalyst of Example 2. Again, the solid points indicate attempts at oxidative regeneration of the catalyst. As will be apparent from the illustration, the Cu/Zn co-precipitated pair (Curve II) became inactivated much more rapidly than did the Cu/Zn/Al co-precipitated catalyst (Curve I) and, in contrast to the Cu/Zn/Al catalyst, was unaffected by attempts at regeneration.

Curve III shows the result obtained with a Cu/Zn co-precipitated pair which has been physically mixed with Al by high-shear slurry technique (Example 3). As before, the solid points indicate attempts at oxidative regeneration. This catalyst is seen to behave very similarly to the Cu/Zn co-precipitated pair of Example 2. Physical mixture of the Al with the Cu/Zn pair does not provide the oxidative regenerability shown by the Cu/Zn/Al co-precipitated catalyst of Example 1.

Having thus described our invention, it is to be understood that there are to be no undue limitations placed thereon by reason of the description and illustrative examples other than those set forth in the following claims.

We claim:

1. A catalyst composition comprising:
   (A) coprecipitated metal components consisting essentially of Cu, Zn and Al wherein the atomic ratio of Al/(Cu+Zn) is greater than or equal to 0.2:1 and the ratio of Cu/Zn is from 0.2:1 to 5.0:1 and
   (B) an acidic dehydrating component.

2. The catalyst composition of claim 1 wherein said acidic dehydrating component is selected from the group consisting of gamma alumina; silica-alumina; clays; natural or synthetically prepared crystalline aluminosilicates; crystalline zeolites having a constraint index within the approximate range of 1–12 and a high silica content; phosphates; and titanium oxide in combination with silicon oxide, rare earths and clays.

3. The catalyst composition of claim 1 wherein said acid dehydrating component comprises from 5 wt % to 95 wt % of said composition.

4. The catalyst composition of claim 3 wherein said component comprises gamma alumina.

5. The composition of claim 1 wherein said atomic ratio of Al/(Cu+Zn) is between 0.2:1 and 2:1.

6. The composition of claim 5 wherein said ratio is between 0.2:1 and 0.7:1.

7. The composition of claim 1 wherein said coprecipitated component has been calcined to oxidize said metals to their respective oxides.

8. The composition of claim 1, 2, 3, 4, 5, 6 or 7 which is oxidatively regenerated by contacting with an oxygen-containing gas at temperatures of between about 250° C. and 540° C.

* * * * *